US012350253B2

(12) United States Patent
Whalley et al.

(10) Patent No.: US 12,350,253 B2
(45) Date of Patent: Jul. 8, 2025

(54) USE OF CANNABINOIDS IN THE TREATMENT OF DYSKINESIA ASSOCIATED WITH PARKINSON'S DISEASE

(71) Applicant: Jazz Pharmaceuticals Research UK Limited, Sittingbourne (GB)

(72) Inventors: Benjamin Whalley, Cambridge (GB); Javier Fernández-Ruiz, Madrid (ES); Rosario Moratalla Villalba, Madrid (ES)

(73) Assignee: JAZZ PHARMACEUTICALS RESEARCH UK LIMITED, Sittingbourne (GB)

( * ) Notice: Subject to any disclaimer, the term of this patent is extended or adjusted under 35 U.S.C. 154(b) by 665 days.

(21) Appl. No.: 17/638,629

(22) PCT Filed: Aug. 25, 2020

(86) PCT No.: PCT/GB2020/052039
§ 371 (c)(1),
(2) Date: Feb. 25, 2022

(87) PCT Pub. No.: WO2021/038219
PCT Pub. Date: Mar. 4, 2021

(65) Prior Publication Data
US 2023/0024312 A1 Jan. 26, 2023

(30) Foreign Application Priority Data
Aug. 27, 2019 (GB) .................................. 1912244

(51) Int. Cl.
*A61K 31/352* (2006.01)
*A61P 25/16* (2006.01)
(52) U.S. Cl.
CPC .............. *A61K 31/352* (2013.01); *A61P 25/16* (2018.01)
(58) Field of Classification Search
CPC ............................... A61K 31/352; A61K 25/16
See application file for complete search history.

(56) References Cited

U.S. PATENT DOCUMENTS

| | | |
|---|---|---|
| 8,632,825 B2 | 1/2014 | Velasco Diez et al. |
| 8,790,719 B2 | 7/2014 | Parolaro et al. |
| 9,017,737 B2 | 4/2015 | Kikuchi et al. |
| 9,125,859 B2 | 9/2015 | Whalley et al. |
| 9,474,726 B2 | 10/2016 | Guy et al. |
| 9,675,654 B2 | 6/2017 | Parolaro et al. |
| 9,949,936 B2 | 4/2018 | Guy et al. |
| 9,949,937 B2 | 4/2018 | Guy et al. |
| 9,956,183 B2 | 5/2018 | Guy et al. |
| 9,956,184 B2 | 5/2018 | Guy et al. |
| 9,956,185 B2 | 5/2018 | Guy et al. |
| 9,956,186 B2 | 5/2018 | Guy et al. |
| 9,962,341 B2 | 5/2018 | Stott et al. |
| 10,039,724 B2 | 8/2018 | Stott et al. |
| 10,092,525 B2 | 10/2018 | Guy et al. |
| 10,098,867 B2 | 10/2018 | Javid et al. |
| 10,111,840 B2 | 10/2018 | Guy et al. |
| 10,137,095 B2 | 11/2018 | Guy et al. |
| 10,220,005 B2 | 3/2019 | Martinez-Orgado et al. |
| 10,226,433 B2 | 3/2019 | Di Marzo et al. |
| 10,583,096 B2 | 3/2020 | Guy et al. |
| 10,603,288 B2 | 3/2020 | Guy et al. |
| 10,653,641 B2 | 5/2020 | Robson et al. |
| 10,709,671 B2 | 7/2020 | Guy et al. |
| 10,709,673 B2 | 7/2020 | Guy |
| 10,709,674 B2 | 7/2020 | Guy et al. |
| 10,729,665 B2 | 8/2020 | Whalley et al. |
| 10,758,514 B2 | 9/2020 | Liu et al. |
| 10,765,643 B2 | 9/2020 | Guy et al. |
| 10,799,467 B2 | 10/2020 | Whalley et al. |
| 10,807,777 B2 | 10/2020 | Whittle |
| 10,849,860 B2 | 12/2020 | Guy et al. |
| 10,918,608 B2 | 2/2021 | Guy et al. |
| 10,966,939 B2 | 4/2021 | Guy et al. |
| 11,000,486 B2 | 5/2021 | Wright et al. |
| 11,065,209 B2 | 7/2021 | Guy et al. |
| 11,065,227 B2 | 7/2021 | Stott et al. |
| 11,096,905 B2 | 8/2021 | Guy et al. |
| 11,147,776 B2 | 10/2021 | Stott et al. |
| 11,147,783 B2 | 10/2021 | Stott et al. |
| 11,154,516 B2 | 10/2021 | Guy et al. |
| 11,154,517 B2 | 10/2021 | Guy et al. |
| 11,160,757 B1 | 11/2021 | Wilkhu et al. |
| 11,160,795 B2 | 11/2021 | Guy et al. |
| 11,207,292 B2 | 12/2021 | Guy et al. |
| 11,229,612 B2 | 1/2022 | Wright et al. |
| 11,291,631 B2 | 4/2022 | Shah |
| 11,311,498 B2 | 4/2022 | Guy et al. |
| 11,318,109 B2 | 5/2022 | Whalley et al. |

(Continued)

OTHER PUBLICATIONS

Carroll, Ph. D., et al., Cannabis for Dyskinesia in Parkinson Disease, 63(7) Neurology 1245-1250 (2004) (Year: 2004).*
U.S. Appl. No. 15/640,033, filed Jun. 30, 2017.
U.S. Appl. No. 16/768,241, filed May 29, 2020.
U.S. Appl. No. 16/959,350, filed Jun. 30, 2020.
U.S. Appl. No. 16/959,354, filed Jun. 30, 2020.
U.S. Appl. No. 16/959,357, filed Jun. 30, 2020.
U.S. Appl. No. 16/935,005, filed Jul. 21, 2020.
U.S. Appl. No. 17/012,448, filed Sep. 4, 2020.
U.S. Appl. No. 17/050,956, filed Oct. 27, 2020.
U.S. Appl. No. 17/102,109, filed Nov. 23, 2020.
U.S. Appl. No. 17/231,625, filed Apr. 15, 2021.
U.S. Appl. No. 17/296,066, filed May 21, 2021.
U.S. Appl. No. 17/296,076, filed May 21, 2021.
U.S. Appl. No. 17/424,682, filed Jul. 21, 2021.
U.S. Appl. No. 17/426,442, filed Jul. 28, 2021.
U.S. Appl. No. 17/406,401, filed Aug. 19, 2021.

(Continued)

*Primary Examiner* — Timothy R Rozof
(74) *Attorney, Agent, or Firm* — COOLEY LLP

(57) ABSTRACT

The present disclosure relates to the use of cannabinoids in the treatment of dyskinesia associated with Parkinson's disease. In particular the cannabinoid is tetrahydrocannabivarin (THCV). Preferably the THCV used is in the form of a botanically derived purified THCV. Alternatively, a synthetically produced THCV is used.

4 Claims, 5 Drawing Sheets

Specification includes a Sequence Listing.

(56) References Cited

U.S. PATENT DOCUMENTS

| | | | |
|---|---|---|---|
| 11,357,741 B2 | 6/2022 | Guy et al. | |
| 11,400,055 B2 | 8/2022 | Guy et al. | |
| 11,406,623 B2 | 8/2022 | Guy et al. | |
| 11,413,266 B2 | 8/2022 | Biró et al. | |
| 11,419,829 B2 | 8/2022 | Whalley et al. | |
| 11,426,362 B2 | 8/2022 | Wright et al. | |
| 11,446,258 B2 | 9/2022 | Guy et al. | |
| 11,590,087 B2 | 2/2023 | Guy et al. | |
| 11,633,369 B2 | 4/2023 | Guy et al. | |
| 11,679,087 B2 | 6/2023 | Guy et al. | |
| 11,684,598 B2 | 6/2023 | Stott et al. | |
| 11,701,330 B2 | 7/2023 | Guy et al. | |
| 11,766,411 B2 | 9/2023 | Guy et al. | |
| 11,793,770 B2 | 10/2023 | Stott et al. | |
| 2012/0004251 A1* | 1/2012 | Whalley | A61P 25/08 514/425 |
| 2015/0359756 A1 | 12/2015 | Guy et al. | |
| 2017/0239193 A1 | 8/2017 | Guy et al. | |
| 2018/0071210 A1 | 3/2018 | Wilkhu et al. | |
| 2018/0228751 A1 | 8/2018 | Stott et al. | |
| 2019/0167583 A1 | 6/2019 | Shah | |
| 2019/0314296 A1 | 10/2019 | Wright et al. | |
| 2019/0321307 A1 | 10/2019 | Guy et al. | |
| 2019/0365667 A1 | 12/2019 | Wright et al. | |
| 2020/0138738 A1 | 5/2020 | Guy et al. | |
| 2020/0179303 A1 | 6/2020 | Guy et al. | |
| 2020/0206153 A1 | 7/2020 | Whalley et al. | |
| 2020/0237683 A1 | 7/2020 | Whalley et al. | |
| 2020/0297656 A1 | 9/2020 | Guy et al. | |
| 2020/0352878 A1 | 11/2020 | Guy et al. | |
| 2021/0015789 A1 | 1/2021 | Guy et al. | |
| 2021/0052512 A1 | 2/2021 | Guy et al. | |
| 2021/0059949 A1 | 3/2021 | Wilkhu et al. | |
| 2021/0059960 A1 | 3/2021 | Wilkhu et al. | |
| 2021/0059976 A1 | 3/2021 | Wilkhu et al. | |
| 2021/0069333 A1 | 3/2021 | Velasco Diez et al. | |
| 2021/0100755 A1 | 4/2021 | Whalley et al. | |
| 2021/0169824 A1 | 6/2021 | Guy et al. | |
| 2021/0177773 A1 | 6/2021 | Guy et al. | |
| 2021/0290565 A1 | 9/2021 | Guy et al. | |
| 2021/0308072 A1 | 10/2021 | Wright et al. | |
| 2021/0330636 A1 | 10/2021 | Guy et al. | |
| 2021/0401771 A1 | 12/2021 | Guy et al. | |
| 2022/0000800 A1 | 1/2022 | Guy et al. | |
| 2022/0008355 A1 | 1/2022 | Guy et al. | |
| 2022/0016048 A1 | 1/2022 | Guy et al. | |
| 2022/0023232 A1 | 1/2022 | Guy et al. | |
| 2022/0040155 A1 | 2/2022 | Guy et al. | |
| 2022/0062197 A1 | 3/2022 | Stott et al. | |
| 2022/0062211 A1 | 3/2022 | Stott et al. | |
| 2022/0087951 A1 | 3/2022 | Knappertz | |
| 2022/0096397 A1 | 3/2022 | Wright et al. | |
| 2022/0168266 A1 | 6/2022 | Guy et al. | |
| 2022/0183997 A1 | 6/2022 | Guy et al. | |
| 2022/0184000 A1 | 6/2022 | Guy et al. | |
| 2022/0202738 A1 | 6/2022 | Guy et al. | |
| 2022/0211629 A1 | 7/2022 | Wilkhu et al. | |
| 2022/0226257 A1 | 7/2022 | Guy et al. | |
| 2022/0233495 A1 | 7/2022 | Silcock et al. | |
| 2022/0249396 A1 | 8/2022 | Guy et al. | |
| 2022/0257529 A1 | 8/2022 | Guy et al. | |
| 2022/0265573 A1 | 8/2022 | Guy et al. | |
| 2022/0288055 A1 | 9/2022 | Silcock et al. | |
| 2022/0378714 A1 | 12/2022 | Guy et al. | |
| 2022/0378715 A1 | 12/2022 | Guy et al. | |
| 2022/0378738 A1 | 12/2022 | Guy et al. | |
| 2022/0387347 A1 | 12/2022 | Whalley et al. | |
| 2022/0395470 A1 | 12/2022 | Whalley et al. | |
| 2022/0395471 A1 | 12/2022 | Guy et al. | |
| 2023/0000789 A1 | 1/2023 | Guy et al. | |
| 2023/0022487 A1 | 1/2023 | Guy et al. | |
| 2023/0026079 A1 | 1/2023 | Guy et al. | |
| 2023/0032502 A1 | 2/2023 | Guy et al. | |
| 2023/0038423 A1 | 2/2023 | Silcock et al. | |
| 2023/0068885 A1 | 3/2023 | Guy et al. | |
| 2023/0143812 A1 | 5/2023 | Knappertz et al. | |
| 2023/0235825 A1 | 7/2023 | Thompson et al. | |
| 2023/0248664 A1 | 8/2023 | Guy | |
| 2023/0263744 A1 | 8/2023 | Guy | |
| 2023/0277560 A1 | 9/2023 | Checketts et al. | |
| 2023/0277561 A1 | 9/2023 | Checketts et al. | |
| 2023/0277562 A1 | 9/2023 | Checketts et al. | |
| 2023/0277563 A1 | 9/2023 | Checketts et al. | |
| 2023/0285419 A1 | 9/2023 | Checketts et al. | |
| 2023/0285420 A1 | 9/2023 | Checketts et al. | |
| 2023/0285421 A1 | 9/2023 | Checketts et al. | |
| 2023/0285422 A1 | 9/2023 | Checketts et al. | |
| 2023/0285423 A1 | 9/2023 | Checketts et al. | |
| 2023/0285424 A1 | 9/2023 | Checketts et al. | |
| 2023/0285425 A1 | 9/2023 | Checketts et al. | |
| 2023/0285426 A1 | 9/2023 | Checketts et al. | |
| 2023/0285427 A1 | 9/2023 | Checketts et al. | |
| 2023/0285428 A1 | 9/2023 | Checketts et al. | |
| 2023/0301934 A1 | 9/2023 | Whalley et al. | |
| 2023/0301936 A1 | 9/2023 | Guy | |
| 2023/0310464 A1 | 10/2023 | Checketts et al. | |

OTHER PUBLICATIONS

U.S. Appl. No. 17/435,892, filed Sep. 2, 2021.
U.S. Appl. No. 17/472,000, filed Sep. 10, 2021.
U.S. Appl. No. 17/548,232, filed Dec. 10, 2021.
U.S. Appl. No. 17/606,370, filed Oct. 25, 2021.
U.S. Appl. No. 17/611,824, filed Nov. 16, 2021.
U.S. Appl. No. 17/529,005, filed Nov. 17, 2021.
U.S. Appl. No. 17/552,487, filed Dec. 16, 2021.
U.S. Appl. No. 17/576,868, filed Jan. 14, 2022.
U.S. Appl. No. 17/585,485, filed Jan. 26, 2022.
U.S. Appl. No. 17/627,946, filed Jan. 18, 2022.
U.S. Appl. No. 17/631,069, filed Jan. 28, 2022.
U.S. Appl. No. 17/689,607, filed Mar. 8, 2022.
U.S. Appl. No. 17/689,245, filed Mar. 8, 2022.
U.S. Appl. No. 17/744,224, filed May 13, 2022.
U.S. Appl. No. 17/705,443, filed Mar. 28, 2022.
U.S. Appl. No. 17/768,048, filed Apr. 11, 2022.
U.S. Appl. No. 17/770,435, filed Apr. 20, 2022.
U.S. Appl. No. 17/770,436, filed Apr. 20, 2022.
U.S. Appl. No. 17/771,184, filed Apr. 22, 2022.
U.S. Appl. No. 17/771,190, filed Apr. 22, 2022.
U.S. Appl. No. 17/771,195, filed Apr. 22, 2022.
U.S. Appl. No. 17/771,183, filed Apr. 22, 2022.
U.S. Appl. No. 17/777,734, filed May 18, 2022.
U.S. Appl. No. 17/777,677, filed May 18, 2022.
U.S. Appl. No. 17/777,681, filed May 18, 2022.
U.S. Appl. No. 17/841,167, filed Jun. 15, 2022.
U.S. Appl. No. 17/786,949, filed Jun. 17, 2022.
U.S. Appl. No. 17/817,753, filed Aug. 5, 2022.
U.S. Appl. No. 17/853,367, filed Jun. 29, 2022.
U.S. Appl. No. 18/002,437, filed Dec. 19, 2022.
U.S. Appl. No. 18/005,838, filed Jan. 17, 2023.
U.S. Appl. No. 18/005,841, filed Jan. 17, 2023.
U.S. Appl. No. 18/005,845, filed Jan. 17, 2023.
U.S. Appl. No. 18/005,843, filed Jan. 17, 2023.
U.S. Appl. No. 18/005,847, filed Jan. 17, 2023.
U.S. Appl. No. 18/005,848, filed Jan. 17, 2023.
U.S. Appl. No. 18/005,851, filed Jan. 18, 2023.
U.S. Appl. No. 18/005,852, filed Jan. 18, 2023.
U.S. Appl. No. 18/005,853, filed Jan. 18, 2023.
U.S. Appl. No. 18/005,959, filed Jan. 18, 2023.
U.S. Appl. No. 18/005,960, filed Jan. 18, 2023.
U.S. Appl. No. 18/005,961, filed Jan. 18, 2023.
U.S. Appl. No. 18/006,125, filed Jan. 19, 2023.
U.S. Appl. No. 18/006,127, filed Jan. 19, 2023.
U.S. Appl. No. 18/006,129, filed Jan. 19, 2023.
U.S. Appl. No. 18/006,131, filed Jan. 19, 2023.
U.S. Appl. No. 18/006,133, filed Jan. 19, 2023.
U.S. Appl. No. 18/006,121, filed Jan. 19, 2023.
U.S. Appl. No. 18/161,603, filed Jan. 30, 2023.
U.S. Appl. No. 18/170,235, filed Feb. 16, 2023.

(56) References Cited

OTHER PUBLICATIONS

U.S. Appl. No. 18/043,810, filed Mar. 2, 2023.
U.S. Appl. No. 18/044,941, filed Mar. 10, 2023.
U.S. Appl. No. 18/245,856, filed Mar. 17, 2023.
U.S. Appl. No. 18/186,792, filed Mar. 20, 2023.
U.S. Appl. No. 18/311,221, filed May 2, 2023.
U.S. Appl. No. 18/320,906, filed May 19, 2023.
U.S. Appl. No. 18/256,307, filed Jun. 7, 2023.
U.S. Appl. No. 18/257,373, filed Jun. 14, 2023.
U.S. Appl. No. 18/257,537, filed Jun. 14, 2023.
U.S. Appl. No. 18/257,479, filed Jun. 14, 2023.
U.S. Appl. No. 18/258,485, filed Jun. 20, 2023.
U.S. Appl. No. 18/446,405, filed Aug. 8, 2023.
U.S. Appl. No. 18/546,254, filed Aug. 11, 2023.
U.S. Appl. No. 18/548,003, filed Aug. 25, 2023.
U.S. Appl. No. 18/477,467, filed Sep. 28, 2023.
U.S. Appl. No. 18/479,671, filed Oct. 2, 2023.
Brotchie, J. M., Adjuncts to Dopamine Replacement: A Pragmatic Approach to Reducing the Problem of Dyskinesia in Parkinson's Disease, Movement Disorders, vol. 13, No. 6, 1998, pp. 871-876.
Carwin, A. & Fernandez, H., Prevalence, Benefits, and Adverse Effects of Cannabis Use in Parkinson's Patients (P3.8-029), Neurology, Apr. 9, 1992 (15 Supplement), 4 pages.
Epidiolex® (cannabidiol) oral solution, CV, Prescribing Information, 2018, 30 pages; https://www.accessdata.fda.gov/drugsatfda_docs/label/2018/210365lbl.pdf.
Espadas, I. et al., Beneficial effects of the phytocannabinoid Δ9-THCV in L-DOPA-induced dyskinesia in Parkinson's disease, Neurobiology of Disease, 141 (2020), 104892, 10 pages. https://doi.org/10.1016/j.nbd.2020.104892.
Ferreira, N. C. J. et al., Cannabidiol and Cannabinoid Compounds as Potential Strategies for Treating Parkinson's Disease and L-DOPA-Induced Dyskinesia, Neurotoxicity Research (2020) 37:12-29. https://doi.org/10.1007/s12640-019-00109-8.
Garcia, C. et al., Symptom-relieving and neuroprotective effects of the phytocannabinoid Δ9-THCV in animal models of Parkinson's disease, British Journal of Pharmacology (2011), 163, 1495-1506. doi:10.1111/j.1476-5381.2011.01278.x.
Gutierrez-Valdez, A. L. et al., The combination of oral ⌊-DOPA/rimonabant for effective dyskinesia treatment and cytological preservation in a rat model of Parkinson's disease and ⌊-DOPA-induced dyskinesia, Behavioural Pharmacology 24:640-652, 2013.
Myers, B. et al., Medical Cannabis in the Treatment of Parkinson's Disease (P2.8-016), Neurology, Apr. 9, 2019, 92 (15 Supplement), 3 pages.
Pertwee, R. G., "The Pharmacology and Therapeutic Potential of Cannabidiol," Cannabinoids, Chapter 3, DiMarzo, V. (Ed.), pp. 32-83 (2004).
Pertwee, R.G., The diverse CB1 and CB2 receptor pharmacology of three plant cannabinoids: Δ9-tetrahydrocannabinol, cannabidiol and Δ9-tetrahydrocannabivarin, British Journal of Pharmacology (2008) 153, 199-215.
Van Der Stelt, M. et al., A role for endocannabinoids in the generation of parkinsonism and levodopa-induced dyskinesia in MPTP-lesioned non-human primate models of Parkinson's disease, The FASEB Journal express article 10.1096/fj.04-3010fje. Published online May 13, 2005, 27 pages.
Venderova, K. et al., Survey on Cannabis Use in Parkinson's Disease: Subjective Improvement of Motor Symptoms, Movement Disorders, vol. 19, No. 9, 2004, 5 pages. Published online Apr. 21, 2004 in Wiley InterScience (www.interscience.wiley.com). doi: 10.1002/mds.20111.

\* cited by examiner

The effect of THCV on motor hyperactivity induced by L-DOPA

The effect of THCV on established L-DOPA-induced dyskinesia at the first peak-dose of L-DOPA

SEQUENCE LISTING

```
<160> NUMBER OF SEQ ID NOS: 15

<210> SEQ ID NO 1
<211> LENGTH: 10
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 1

Gly Tyr Thr Phe Thr Ser Ser Tyr Ile Asn
1               5                   10

<210> SEQ ID NO 2
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Thr Ile Asn Pro Val Ser Gly Ser Thr Ser Tyr Ala Gln Lys Phe Gln
1               5                   10                  15

Gly

<210> SEQ ID NO 3
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Gly Gly Trp Phe Asp Tyr
1               5

<210> SEQ ID NO 4
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Thr Gly Thr Ser Ser Asp Val Gly Ser Tyr Asn Tyr Val Asn
1               5                   10

<210> SEQ ID NO 5
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Leu Met Ile Tyr Gly Val Ser Lys Arg Pro Ser
1               5                   10

<210> SEQ ID NO 6
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 6

Gly Thr Phe Ala Gly Gly Ser Tyr Tyr Gly
1               5                   10

<210> SEQ ID NO 7
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Tyr Val Asn Trp Tyr Gln Gln His Pro Gly Lys Ala Pro Lys Leu
        35                  40                  45

Met Ile Tyr Gly Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Thr Phe Ala Gly Gly
                85                  90                  95

Ser Tyr Tyr Gly Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 8
<211> LENGTH: 445
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

-continued

Tyr Ile Asn Trp Val Arg Gln Ala Pro Gly Gln Gly Leu Glu Trp Met
             35                  40                  45

Gly Thr Ile Asn Pro Val Ser Gly Ser Thr Ser Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Gly Gly Trp Phe Asp Tyr Trp Gly Gln Gly Thr Leu Val Thr
                100                 105                 110

Val Ser Ser Ala Ser Thr Lys Gly Pro Ser Val Phe Pro Leu Ala Pro
             115                 120                 125

Ser Ser Lys Ser Thr Ser Gly Gly Thr Ala Ala Leu Gly Cys Leu Val
         130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                 165                 170                 175

Leu Tyr Ser Leu Ser Ser Val Val Thr Val Pro Ser Ser Ser Leu Gly
             180                 185                 190

Thr Gln Thr Tyr Ile Cys Asn Val Asn His Lys Pro Ser Asn Thr Lys
         195                 200                 205

Val Asp Lys Arg Val Glu Pro Lys Ser Cys Asp Lys Thr His Thr Cys
210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                 245                 250                 255

Val Thr Cys Val Val Val Asp Val Ser His Glu Asp Pro Glu Val Lys
             260                 265                 270

Phe Asn Trp Tyr Val Asp Gly Val Glu Val His Asn Ala Lys Thr Lys
         275                 280                 285

Pro Arg Glu Glu Gln Tyr Asn Ser Thr Tyr Arg Val Val Ser Val Leu
     290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                 325                 330                 335

Ala Lys Gly Gln Pro Arg Glu Pro Gln Val Tyr Thr Leu Pro Pro Ser
             340                 345                 350

Arg Glu Glu Met Thr Lys Asn Gln Val Ser Leu Thr Cys Leu Val Lys
         355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                 405                 410                 415

Gln Gly Asn Val Phe Ser Cys Ser Val Met His Glu Ala Leu His Asn
             420                 425                 430

His Tyr Thr Gln Lys Ser Leu Ser Leu Ser Pro Gly Lys
         435                 440                 445

<210> SEQ ID NO 9
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 9

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Tyr Val Asn Trp Tyr Gln Gln His Pro Gly Lys Ala Pro Lys Leu
        35                  40                  45

Met Ile Tyr Gly Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Thr Phe Ala Gly Gly
                85                  90                  95

Ser Tyr Tyr Gly Val Phe Gly Gly Gly Thr Lys Leu Thr Val Leu
            100                 105                 110

<210> SEQ ID NO 10
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Tyr Ile Asn Trp Val Arg Gln Ala Pro Gly Gln Gly Leu Glu Trp Met
        35                  40                  45

Gly Thr Ile Asn Pro Val Ser Gly Ser Thr Ser Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Trp Phe Asp Tyr Trp Gly Gln Gly Thr Leu Val Thr
            100                 105                 110

Val Ser Ser
        115

<210> SEQ ID NO 11
<211> LENGTH: 6
<212> TYPE: PRT
<213> ORGANISM: Homo sapiens

<400> SEQUENCE: 11

Trp Leu Asp Asp Phe Asn
1               5

```
<210> SEQ ID NO 12
<211> LENGTH: 9
<212> TYPE: PRT
<213> ORGANISM: Homo sapiens

<400> SEQUENCE: 12

Gly Cys Trp Leu Asp Asp Phe Asn Cys
1               5

<210> SEQ ID NO 13
<211> LENGTH: 11
<212> TYPE: PRT
<213> ORGANISM: Homo sapiens

<400> SEQUENCE: 13

Lys Gly Cys Trp Leu Asp Asp Phe Asn Cys Tyr
1               5                   10

<210> SEQ ID NO 14
<211> LENGTH: 5
<212> TYPE: PRT
<213> ORGANISM: Homo sapiens

<400> SEQUENCE: 14

Glu Gln Asp Lys Arg
1               5

<210> SEQ ID NO 15
<211> LENGTH: 15
<212> TYPE: PRT
<213> ORGANISM: Homo sapiens

<400> SEQUENCE: 15

Cys Glu Gly Glu Gln Asp Lys Arg Leu His Cys Tyr Ala Ser Trp
1               5                   10                  15
```

USE OF CANNABINOIDS IN THE TREATMENT OF DYSKINESIA ASSOCIATED WITH PARKINSON'S DISEASE

CROSS-REFERENCE TO RELATED APPLICATIONS

This application claims the benefit of International PCT Application No. PCT/GB2020/052039, filed Aug. 25, 2020; and Great Britain Application No. 1912244.9, filed Aug. 27, 2019; each of the aforementioned applications are incorporated herein by reference in its entirety.

FIELD OF THE INVENTION

The present invention relates to the use of cannabinoids in the treatment of dyskinesia associated with Parkinson's disease. In particular the cannabinoid is tetrahydrocannabivarin (THCV).

Preferably the THCV used is in the form of a botanically derived purified THCV. Alternatively, a synthetically produced THCV is used.

BACKGROUND TO THE INVENTION

Parkinson's disease (PD) is a progressive neurodegenerative disorder, the major clinical symptoms in PD are tremor, bradykinesia, postural instability and rigidity. These symptoms that result from the severe dopaminergic denervation of the striatum caused by the progressive death of dopaminergic neurons of the substantia nigra pars compacta. Major symptoms in PD such as bradykinesia can be attenuated with dopaminergic replacement therapy using the dopamine precursor levodopa or L-DOPA. However, this therapy does not work in all PD patients and when used for more than 5-10 years, the L-DOPA loses efficacy and provokes an irreversible dyskinetic state characterized by the appearance of abnormal involuntary movements.

Dyskinesia is a category of movement disorders that are characterised by involuntary muscle movements. These movements include tics or chorea and diminished voluntary movements. Examples of dyskinesia include slight hand tremors and uncontrolled upper or lower body twitches.

Levodopa-induced dyskinesia (LID) commonly appears first in the foot of the most affected side of the body. Treatment options for LID include the use of levetiracetam; nicotine; deep brain stimulation; and mavoglurant which is the first FDA approved drug for this condition.

Therefore, the search of novel symptomatic therapies devoid of pro-dyskinetic side effects or able to delay/reduce these signs, as well as of neuroprotective treatments effective in delaying the progression of nigrostriatal damage in PD, remain as the major challenges in PD therapy.

Cannabinoid-based compounds have been recently proposed as promising therapies in PD given their potential as symptom-alleviating and disease-modifying agents. As regards to the first of these two options, the blockade of cannabinoid receptor type-1 (CB1), which is highly abundant in basal ganglia structures, may be effective in reducing the motor inhibition typical of PD patients, which is concordant with the overactivity of the cannabinoid system observed in PD patients and animal models of this disease.

However, the preclinical studies conducted so far have demonstrated that the efficacy of CB1 receptor blockade was restricted to specific circumstances, e.g. the use of low doses, strong nigral damage, conditions that were not reproduced in the only clinical trial conducted so far with a CB1 receptor blocker, which included a population of patients that were all good-responders to L-DOPA. Therefore, this potential therapeutic strategy merits further clinical investigation, this time with PD patients that respond poorly to L-DOPA (approximately 15-20% of patients are poor responders to L-DOPA and it appears that, in general, they may correspond to those having tremor as the key symptom rather than rigidity and bradykinesia.

Some cannabinoids have been reported to be also able to protect nigral neurons from death caused by different insults in various experimental models of PD. These include the phytocannabinoids, tetrahydrocannabinol (THC) and cannabidiol (CBD), the synthetic cannabinoid receptor agonist CP55,940 and the anandamide analog AM404.

In addition, acute treatment with the cannabinoid tetrahydrocannabivarin (THCV) was found to be efficacious in reducing motor inhibition in parkinsonian rats, with a potency equivalent to rimonabant. These effects were found to be dopamine-independent and associated with changes in glutamatergic transmission in key structures of the basal ganglia (Garcia et al. 2011). The document does not appear to disclose the origin of THCV nor the purity of THCV.

In 2004, a survey conducted by Venderova et al. looked at the use of cannabis in Parkinson's disease. It was found that after cannabis use, 12 out of 85 patients (14.1%) reported an improvement of LID. There is no disclosure nor even any suggestion of the composition of the cannabis used. Further, there is no mention of THCV let alone the purity of THCV in the cannabis extract used.

Another survey by Carwin et al. in 2019 studied the efficacy and adverse effects of cannabis use in Parkinson's disease patients and found that of the 13 patients 27.3% reported an improvement in dyskinesia. Again, the composition of cannabis used is not disclosed, nor is the presence of THC in the cannabis suggested. Myers et al. discloses a similar study on the use of cannabis in Parkinson's disease patients.

Van der Stelt et al. published a study where it was found that signaling by endocannabinoids contributes to the pathophysiology of Parkinson's disease and LID. There is no mention nor any suggestion of THCV much less the purity of THCV.

Gutierrez-Valdez et al. discloses a study examining the behavioural and cytological effects of oral coadministration of L-DOPA and rimonabant in a 6-hydroxydopamine rat model of Parkinson's disease. It was found that coadministration decreased abnormal involuntary movements and dystonia. The document does not disclose nor suggest THCV let alone the purity of THCV that may be used.

The present invention demonstrates the ability of a low dose of THCV to act as an anti-dyskinetic agent. It has been demonstrated that treatment with THCV administered daily in parallel to L-DOPA was associated with a delay in the appearance of dyskinetic movements. In addition, THCV was also shown to be beneficial in the reduction of dyskinetic signs when administered once the L-DOPA-induced dyskinesia is already established.

BRIEF SUMMARY OF THE DISCLOSURE

In accordance with a first aspect of the present invention there is provided tetrahydrocannabivarin (THCV) for use in the treatment of dyskinesia associated with Parkinson's disease.

Preferably the dose of THCV is between 0.1 and 1000 mg/kg day.

Preferably the THCV is botanically derived highly purified THCV.

Alternatively, the THCV is synthetic THCV.

In a further embodiment the THCV is used to prevent dyskinesia in Parkinson's disease.

In accordance with a second aspect of the present invention there is provided a method of treating a subject suffering from dyskinesia associated with Parkinson's disease comprising administering tetrahydrocannabivarin (THCV) to the subject in need thereof.

Preferably the subject is a mammal, more preferably the mammal is a human.

BRIEF DESCRIPTION OF THE DRAWINGS

Embodiments of the invention are further described hereinafter with reference to the accompanying drawings, in which.

Figure 1:
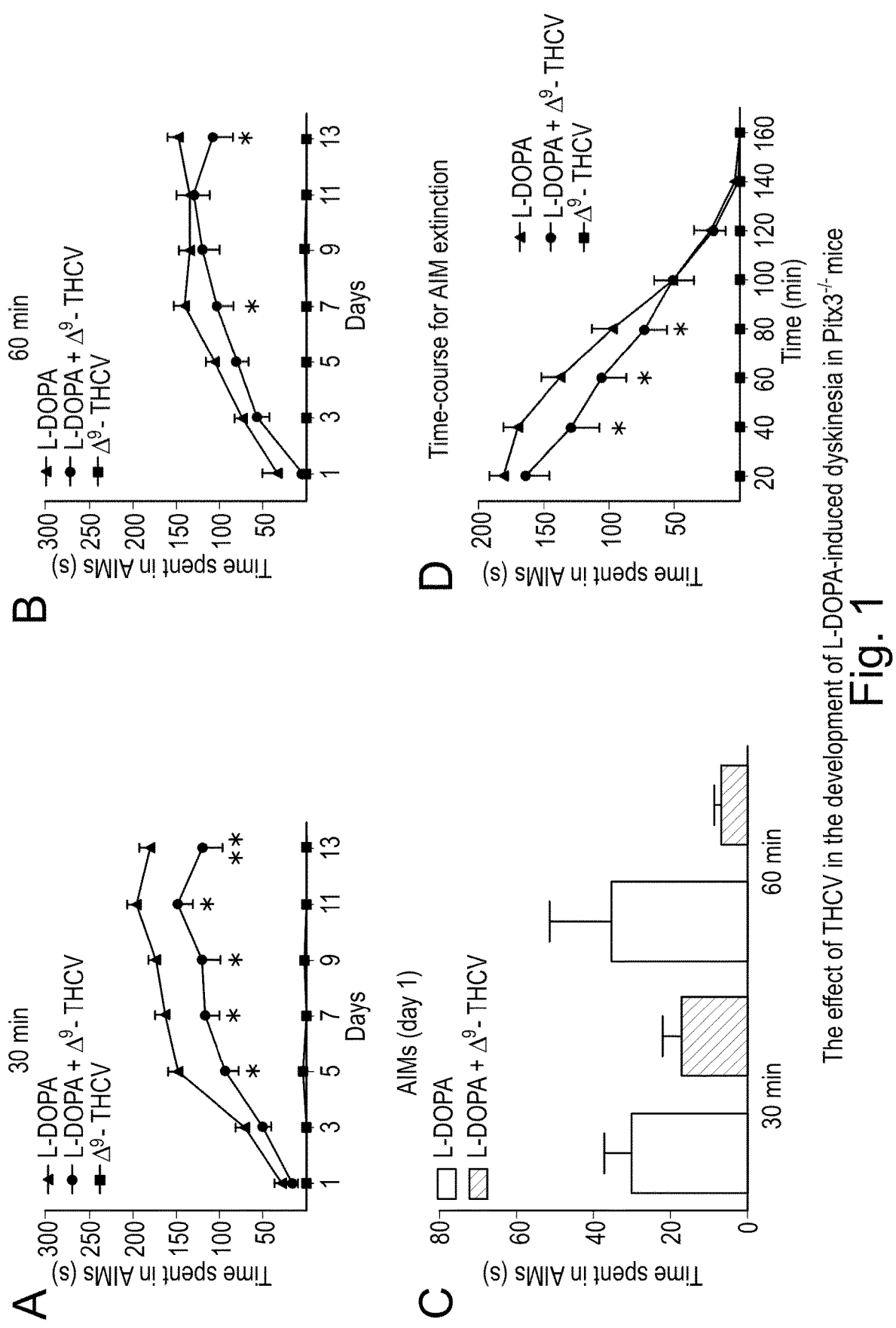
FIG. 1 shows the effect of THCV in the development of L-DOPA-induced dyskinesia in Pitx3$^{-/-}$ mice.

The legends to the figures are described in more details below:

FIG. 1. Chronic THCV treatment attenuates dyskinesia at 30 min (A) and, to a lesser extent, at 60 min (B) post-L-DOPA. A two-way ANOVA with repeated measures followed by the Bonferroni test showed significant differences at 30 min (treatment: $F(2,259)=133.3$, $p<0.0001$; time: $F(6,259)=15.10$, $p<0.0001$; interaction: $F(12,259)=4.14$, $p<0.0001$) and 60 min (treatment: $F(2,259)=77.53$, $p<0.0001$; time: $F(6,259)=7.83$, $p<0.0001$; interaction: $F(12,259)=2.09$, $p<0.05$). C. The acute co-treatment with THCV and L-DOPA decreases, but not significantly using an one-way ANOVA followed by the Bonferroni test ($F(3,71)=1.712$, $p=0.173$), the dyskinesias score at 30 min and 60 min on the day 1 of treatment. D. The kinetic profile of dyskinetic symptoms was evaluated once every 20 min over 160 min on day 13 of the L-DOPA treatment. A two-way ANOVA with repeated measures followed by the Bonferroni test showed significant differences (treatment: $F(2,296)=64.49$, $p<0.0001$; time: $F(7,296)=24.43$, $p<0.0001$; interaction: $F(14,296)=6.39$, $p<0.0001$). The data are expressed as the mean±SEM; *$p<0.05$, **$p<0.01$ versus L-DOPA alone; n=10-19 for each treatment.

Figure 2:
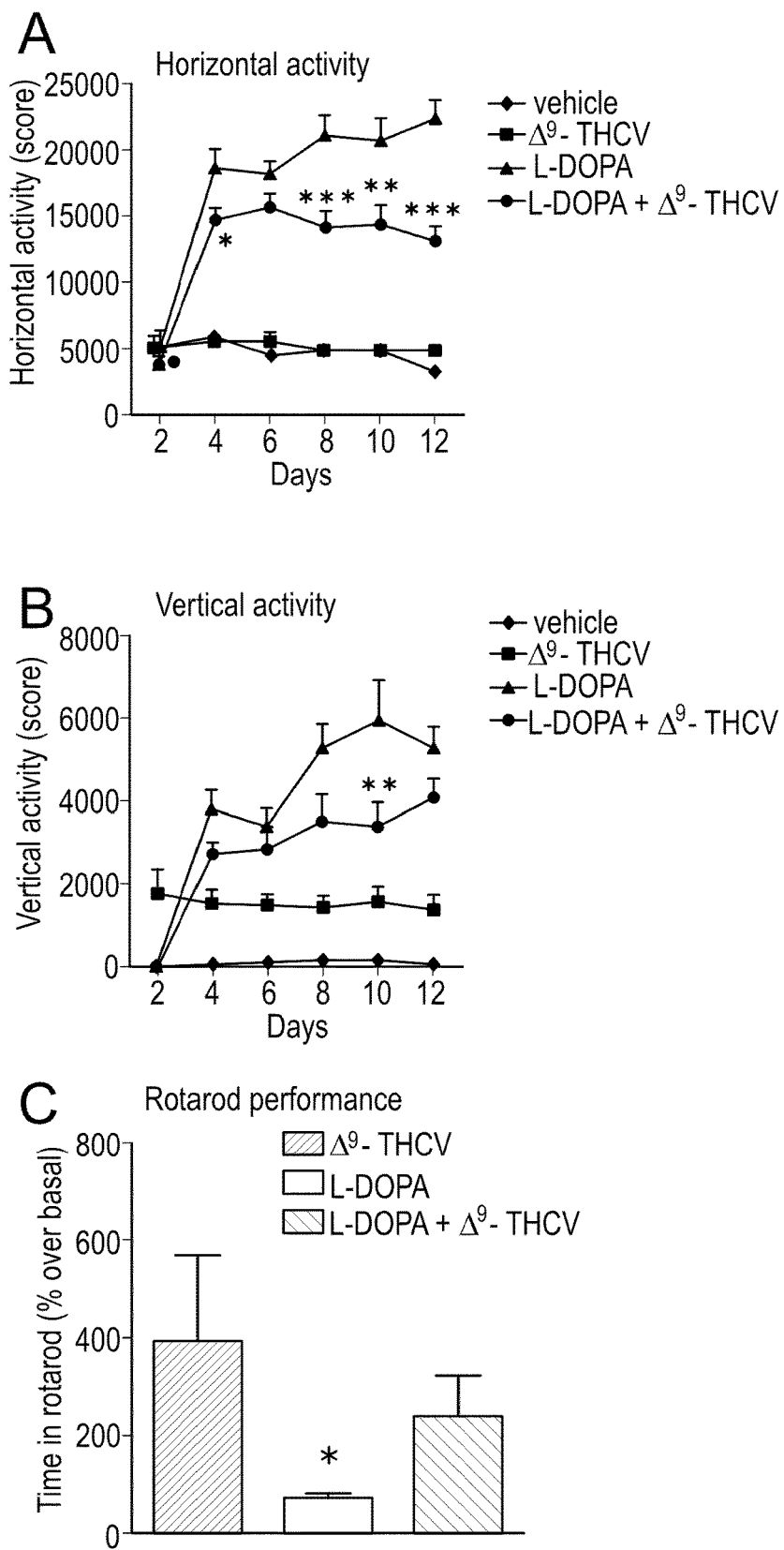
FIG. 2 shows the effect of THCV on motor hyperactivity induced by L-DOPA.

FIG. 2. Horizontal (A) and vertical (B) motor activities were measured in a multicage activity meter system 60 min after L-DOPA or vehicle challenge. A two-way ANOVA with repeated measures followed by the Bonferroni test showed significant differences for the horizontal (treatment: $F(3,252)=100.2$, $p<0.0001$; time: $F(5,252)=12.34$, $p<0.0001$; interaction: $F(15,252)=5.25$, $p<0.0001$) and vertical (treatment: $F(3,252)=37.73$, $p<0.0001$; time: $F(5,252)=6.84$, $p<0.0001$; interaction: $F(15,252)=2.80$, $p<0.0005$) activities. The data are expressed as the mean±SEM; *$p<0.05$, $p<0.01$, *$p<0.001$ versus L-DOPA. C. The Pitx3$^{-/-}$ mice treated with THCV treatment have improved motor coordination in rotarod compared to mice treated with L-DOPA. A one-way ANOVA followed by the Bonferroni test showed significant differences ($F(2,41)=3.858$, $p<0.0001$). The data are expressed as the mean±SEM of percentage of increment of latency to fall regard to the base line execution. *$p<0.05$ versus THCV groups.

Figure 3:
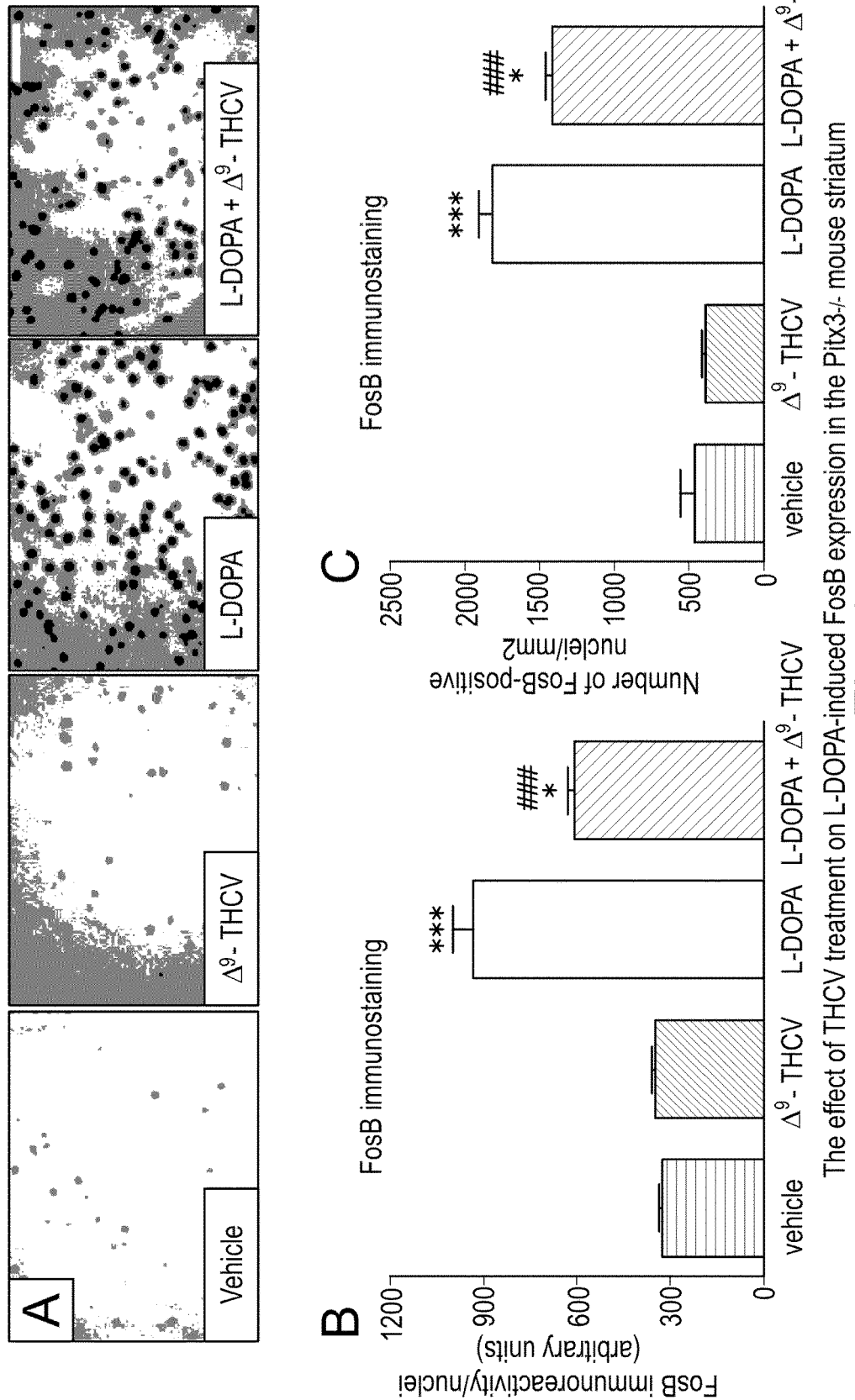
FIG. 3 shows the effect of THCV treatment on L-DOPA-induced FosB expression in the Pitx3$^{-/-}$ mouse striatum.

FIG. 3. A. High-power microphotographs of striatal sections from Pitx3$^{-/-}$ mice illustrating the effect of chronic THCV treatment on L-DOPA-induced FosB expression. B. Striatal quantification of FosB-positive cells after different treatments. The THCV challenge attenuates the increased expression of FosB-positive cells prior to chronic L-DOPA treatment. Histograms represent the number of FosB nuclei. C. In addition, the THCV chronic treatment attenuates the immunostaining-intensity of FosB positive nuclei. Histograms represent a comparative of immunostaining-intensity in a relative scale. The mean±SEM values were analysed by one-way ANOVA followed by the Bonferroni test, and significant differences were found (immunoreactivity: $F(3,25)=17.5$, $p<0.0001$; positive nuclei: $F(3,25)=17.6$, $p<0.0001$). *$p<0.05$, ***$p<0.005$ versus vehicle and THCV groups; ###$p<0.005$ versus L-DOPA+THCV. Scale bar=50 µm.

Figure 4:
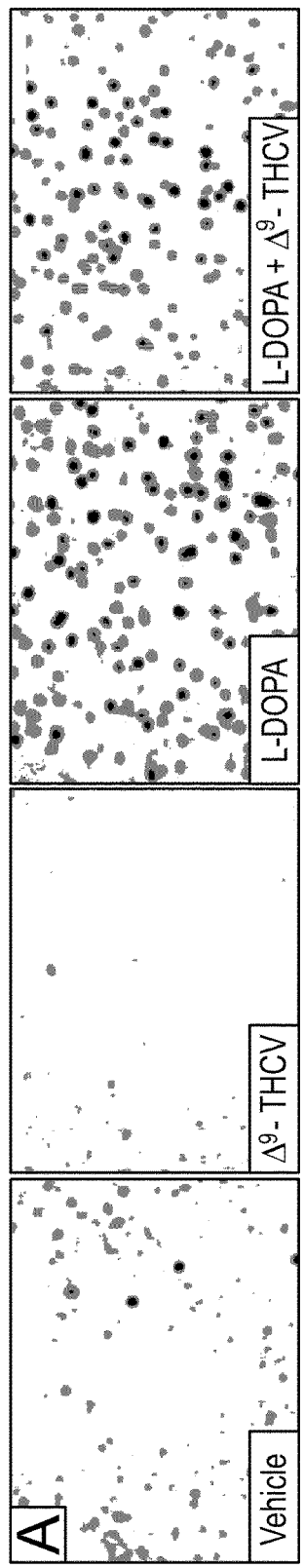
FIG. 4 shows the effect of treatment with THCV on L-DOPA-induced pAcH3 expression in the Pitx3$^{-/-}$ mouse striatum.
Figure 4:
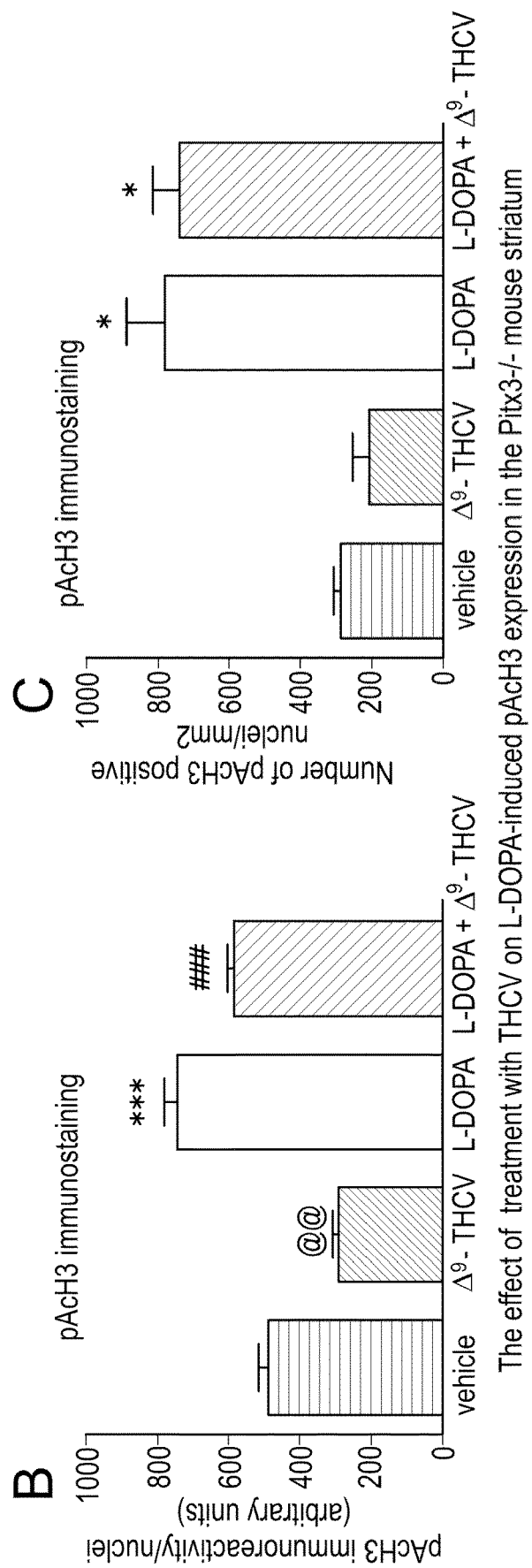

FIG. 4. A. High-power microphotographs of the striatal sections of Pitx3$^{-/-}$ mice illustrating the effect of chronic THCV treatment on pAcH3 expression induced by L-DOPA. B. Striatal quantification of pAcH3-positive cells after different treatments. Histograms represent the density of positive nuclei in mm$^2$. C. Immunostaining intensity of positive pAcH3 nuclei in mouse striatum. The THCV effect decreases the intensity of nuclei in the striatum of Pitx3$^{-/-}$ induced by L-DOPA chronic treatment. The mean±SEM values were analysed by a one-way ANOVA followed by the Bonferroni test, and significant differences were found (immunoreactivity: $F(3,24)=28.86$, $p<0.0001$; positive nuclei: $F(3,24)=6.62$, $p<0.005$). *$p<0.05$, ***$p<0.005$ versus vehicle and THCV groups; @@$p<0.01$ versus vehicle; ###$p<0.005$ versus THCV alone and L-DOPA+THCV. Scale bar=50 µm.

Figure 5:
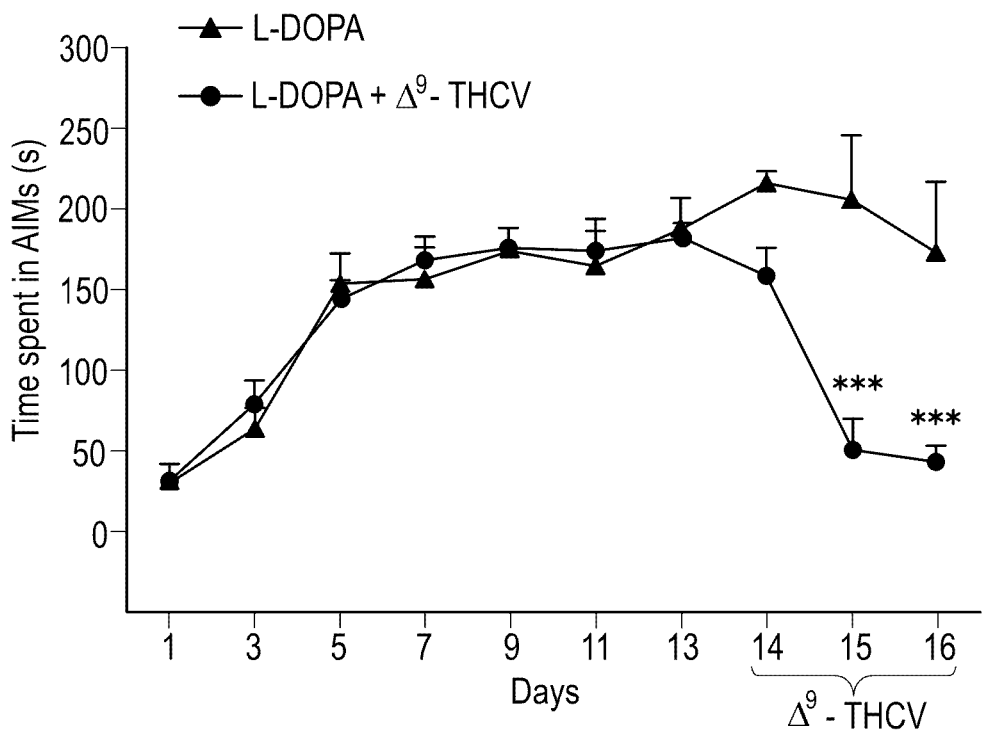
FIG. 5 shows the effect of THCV on established L-DOPA-induced dyskinesia at the first peak-dose of L-DOPA.

FIG. 5. Pitx3$^{-/-}$ mice received daily injections of L-DOPA for 13 days to establish dyskinetic status. On day 14, animals received THCV or vehicle 10 min after L-DOPA injection. The THCV treatment significantly reduced dyskinesia at 30 min post-L-DOPA. The data are expressed as the mean±SEM. Two-way ANOVA followed by the Bonferroni test showed significant differences (treatment: $F(1,166)=14.17$, $p<0.0005$; time: $F(9,166)=15.75$, $p<0.0001$; interaction: $F(9,166)=5.54$, $p<0.0001$). ***$p<0.005$ versus L-DOPA; n=10 for each group.

DETAILED DESCRIPTION

Example 1 below describes the effect of the cannabinoid THCV in a mouse model of L-DOPA induced dyskinesia in Parkinson's disease, using Pitx3$^{-/-}$ mice. The study was undertaken in two parts; firstly the Pitx3$^{-/-}$ mice were evaluated to determine whether THCV was able to delay the appearance of L-DOPA-induced dyskinetic signs and secondly the anti-dyskinetic potential of THCV was explored by investigating whether, in addition to its capability to delay the appearance of dyskinetic signs, it was also effective in attenuating the extent of dyskinesia when administered once these signs were already present.

The THCV used in these studies was botanically derived highly purified THCV with a purity of greater than 95% (w/w). However, such data are representative of THCV from a synthetic origin.

Example 1: Effect of THCV in an Experimental Model of L-Dopa-Induced Dyskinesia in Parkinson's Disease Materials and Methods Animals and Drug Treatments Pitx3$^{-/-}$ aphakia mice and their wildtype littermates, were genotyped using PCR amplification analysis of tail-tip DNA extracts. Mice were housed under a 12 h dark/light cycle with free access to food and water. They were used for experimental purposes at the age of 4-6 month-old (24-30 g of weight).

In a first experiment, animals were treated with an i.p. injection of 10 mg/kg of benserazide hydrochloride followed 20 minutes later by a second i.p. injection of 10 mg/kg of L-DOPA methyl ester. Separate groups of animals received equivalent injections with vehicle (saline) used as controls. Both L-DOPA- and vehicle-treated mice received, 10 minutes after the second injection, a third i.p. injection of THCV (2 mg/kg) or vehicle (Tween 80-saline). The same treatment schedule was repeated daily during approximately two weeks.

In a second experiment, benserazide and L-DOPA (and their corresponding vehicles) were administered to mice following the same schedule than in the previous experiment, but THCV, again at the dose of 2 mg/kg, was given for the first time after approximately two weeks of daily benserazide/L-DOPA treatment, with the administration of the three compounds (and vehicles) extending for at least 3 days.

Behavioural Measurements

Abnormal Involuntary Movements (AIMs):

AIMs were assessed 30 and 60 min after L-DOPA administration. Dyskinesia was scored off-line by a blind rater based on video footage. Ratings were assessed for four minutes at each time point.

Total dyskinesia was rated by adding the duration in seconds of all three-paw and four-paw dyskinetic bouts. Additionally, on odd days, individual mice were placed in actimeters and motor activity was assessed following drug administration.

On Day 14, we evaluated AIMs every 20 min for 160 min after administering L-DOPA to determine the extinction of this response.

Locomotor Activity:

Horizontal and vertical activities were recorded, using a multicage activity meter system consisting of a set of 8 individual cages measuring 20×20×28 cm. Animals were introduced in the actimeter 60 minutes after L-DOPA injection and were assessed for 30 minutes. Horizontal movement was detected by 2 arrays of 16 infrared beams, whereas a third array positioned 4 cm above the floor detected vertical movement.

The software is capable of differentiating between repetitive interruptions of the same photobeam and interruptions of adjacent photobeams. The latter measure was used as an index of ambulatory activity.

Rotarod Test:

Motor coordination was tested using a rotarod. The rotarod was set at a constant speed (10 revolutions per minute) and latency to fall from the rod was assessed. Cut off time was 180 seconds. Before testing, mice were previously habituated in one training session, as described previously.

Sampling and Tissue Preparation:

Following behavioral analysis, animals were euthanized 1 hour after the last injection of L-DOPA. The brains were post-fixed for 24 h and were then transferred to a solution of 0.1 M phosphate buffer containing 0.02% sodium azide for storage at 4° C. To obtain regular blocks, brains were further immersed in 3% agarose and cut in coronal sections (30 μm thick) using a vibratome.

Immunohistochemistry:

Immunostaining was carried out in free-floating sections using a standard avidin-biotin immunocytochemical protocol with the following rabbit antisera: (i) FosB (1:7500), and (ii) anti phospho(Ser10)-acetyl (Lys14)-Hystone 3 (pAcH3; 1:500).

After incubation with primary antibody (overnight), the sections were washed and incubated with biotinylated secondary anti-rabbit antibody (1:500) for 1 h at room temperature. After washing, the sections were incubated with streptavidin for 1 h and antibody staining was developed using DAB.

After developing the reaction, stained sections were mounted, dried, dehydrated, and coverslipped with Permount mounting medium.

For immunostaining quantification in the completely denervated area, we used the Neurolucida software. The borders of the areas of interest in lesioned striatum (complete dorsal striatum and FosB-ir stained dorsal striatum) were outlined from a live image with a 5× objective. The images were then exported to Neuroexplorer to determine the total striatal area and the relative area of FosB-ir stained striatum.

Data are expressed as the % of FosB-ir striatal area in relation to total striatal area.

Regarding the quantification of FosB and pAcH3 immunoreactivity, it was carried out using an image analysis system.

For all sides, immunostaining intensity and number of immunolabeled nuclei were determined using five serial rostrocaudal sections per animal and three counting frames (dorsal, dorsolateral and lateral) per section (0.091 mm2 each frame). Images were digitized with Leica microscope under 40× lens. Before counting, images were thresholded at a standardized grey-scale level. The data are presented as number of stained nuclei per mm$^2$ (mean±standard error of the mean) in the lesioned striatum.

Statistical Analysis:

Data were normally distributed (tested with the Shapiro-Wilk normality test) and were assessed by one-way or two-way (with repeated measures) analysis of variance, as required (see specific test used in the legends to figures), followed by the Bonferroni test, using the GraphPad Prism® software (version 5.01).

Results

Development of L-DOPA-Induced Dyskinesia in Pitx3$^{-/-}$ Mice:

Chronic treatment with L-DOPA of Pitx3$^{-/-}$ mice resulted in the progressive appearance of Abnormal involuntary movements (AIMs), including front paw, hind paw, three-paw, and four-paw dyskinetic movements as shown in FIG. 1.

As a measure of the intensity of dyskinesia the three- and four-paw dyskinetic movements were measured 30 and 60 min after administering L-DOPA (FIG. 1A, 1B). They were already evident after the first injection of L-DOPA (FIG. 1C) and their frequency was significantly elevated during the first week of treatment (FIG. 1A, 1B).

After the first week, the frequency of the dyskinetic movements remained stable for the rest of the chronic treatment (FIG. 1A, 1B).

On the last treatment day, a time-course to determine the extinction of dyskinetic movements was undertaken. This revealed that AIMs were present for at least 2 hours after administering L-DOPA (FIG. 1D).

The dyskinetic profile shown by Pitx3$^{-/-}$ mice after a chronic treatment with L-DOPA also included elevated horizontal and vertical activities measured in a computer-aided actimeter (FIG. 2A, 2B). The elevation was found after four days of chronic L-DOPA treatment, and it remained up to the second week of treatment (FIG. 2A, 2B). A marked deterioration in rotarod performance was also evident after 12 days of daily L-DOPA treatment in Pitx3$^{-/-}$ mice (FIG. 2C).

L-DOPA-Induced Dyskinesia in Pitx3$^{-/-}$ Mice:

In the first study Pitx3$^{-/-}$ mice were evaluated to determine whether THCV was able to delay the appearance of L-DOPA-induced dyskinetic signs.

The co-administration of THCV together with L-DOPA reduced the duration of AIMs (three/four-paw dyskinetic movements) measured at 30 min post-L-DOPA administration, except for days 1 (see FIG. 1C for more details) and 3 of treatment (FIG. 1A).

This effect was more modest when analysed at 60 minutes after L-DOPA administration, with significant differences only at days 7 and 13 of treatment (FIG. 1B).

On the last day of treatment, the differences between animals treated with L-DOPA and THCV and those treated with L-DOPA alone remained up to 80 minutes post-treatment (FIG. 1D).

Importantly, treatment of Pitx3$^{-/-}$ mice with THCV alone showed no dyskinetic movements (FIG. 1A, 1B).

The co-administration of THCV with L-DOPA also improved the deteriorated rotarod performance observed after 12 days of daily L-DOPA treatment (FIG. 2C), as well attenuating the elevated horizontal and vertical activities found in L-DOPA-treated Pitx3$^{-/-}$ mice (FIG. 2A,2B).

Treatment with THCV alone demonstrated no effect on the horizontal activity compared to Pitx3$^{-/-}$ mice treated with vehicle (FIG. 2A), THCV administered alone to these mice did elevate vertical activity by itself, although this elevation did not reach the level of the animals treated with L-DOPA (FIG. 2B).

Striatal Molecular Markers in L-DOPA-Induced Dyskinesia in Pitx3$^{-/-}$ Mice.

The elevation in both striatal molecular markers was observed using immunostaining in L-DOPA-treated Pitx3$^{-/-}$ mice (FIGS. 3 and 4). Both responses were significantly attenuated after the co-administration of L-DOPA and THCV (FIGS. 3 and 4). In the case of FosB, the THCV-induced reduction affected both the number and the immunostaining intensity of FosB-positive cells compared to the chronic L-DOPA-treated mice (FIG. 3), whereas the beneficial effects in the case of pACH3 were only evident in the intensity of immunostained-nuclei (FIG. 4).

Magnitude of L-DOPA-Induced Dyskinesia in Pitx3$^{-/-}$ Mice:

The second study explored the anti-dyskinetic potential of THCV by investigating whether, in addition to its capability to delay the appearance of dyskinetic signs, THCV was also effective in attenuating the extent of dyskinesia when administered once these signs were already present.

THCV treatment was initiated approximately two weeks after the onset of L-DOPA treatment. As shown in FIG. 5, animals chronically treated with L-DOPA developed a progressive elevation in AIMs (in general, similar to the data presented in FIG. 1A) up to day 13 (FIG. 5).

The distribution of these mice in two groups at this time, one in which the treatment with L-DOPA was continued and the other co-treated with L-DOPA and Δ9-THCV, revealed that this cannabinoid was also active in reducing the duration of L-DOPA-induced three/four-paw dyskinesia 30 min after the L-DOPA injection, in comparison with the group that received L-DOPA alone, and this persisted for 3 days (FIG. 5).

CONCLUSIONS

These data show for the first time that the cannabinoid THCV is able to both delay the occurrence of dyskinesia and attenuate the magnitude of the dyskinetic symptoms once they occur.

Such data are of great significance to patients with Parkinson's disease as treatment with THCV may enable a novel therapeutic option.

REFERENCES

1. Garca et al. (2011) "Symptom-relieving and neuroprotective effects of the phytocannabinoid Li9-THCV in animal models of Parkinson's disease." British journal of pharmacology; vol. 163, No. 7.
2. Venderova et al. (2004) "Survey on Cannabis Use in Parkinson's Disease: Subjective Improvement of Motor Symptoms." Movement Disorders; vol. 19; No. 9.
3. Carwin et al. (2019) "Prevalence, Benefits, and Adverse Effects of Cannabis Use in Parkinson's Patients (P3.8-029)." Neurology; vol. 92; No. 15.
4. Myers et al. (2019) "Medical Cannabis in the Treatment of Parkinson's Disease (P2.8-016)." Neurology; vol. 92; No. 15.
5. Van der Stelt et al. (2005) "A role for endocannabinoids in the generation of parkinsonism and levodopa-induced dyskinesia in MPTPlesioned non-human primate models of Parkinson's disease." The FASEB Journal; vol. 19; No. 9.
6. Gutierrez-Valdez et al. (2013) "The combination of oral L.DOPA/rimonabant for effective dyskinesia treatment and cytological preservation in a rat model of Parkinson's disease and L-DOPA-induced dyskinesia." Behavioural Pharmacology; vol. 24; No. 8.

The invention claimed is:

1. A method of treating dyskinesia associated with Parkinson's disease comprising administering a therapeutically effective amount of Tetrahydrocannabivarin (THCV).

2. The method of claim 1, wherein the therapeutically effective amount of THCV is between 0.1 and 1000 mg/kg day.

3. The method of claim 1, wherein the THCV is botanically derived highly purified THCV.

4. The method of claim 1, wherein the THCV is synthetic THCV.

* * * * *